(12) United States Patent
Dahne et al.

(10) Patent No.: US 7,939,103 B2
(45) Date of Patent: May 10, 2011

(54) METHOD FOR PRODUCING CORE-SHELL (CS) PARTICLES AND MICROCAPSULES USING POROUS TEMPLATES, CS PARTICLES AND MICROCAPSULES, AND THE USE THEREOF

(75) Inventors: Lars Dahne, Berlin (DE); Barbara Baude, Schwielowsee (DE)

(73) Assignee: Capsulution Pharma AG, Berlin (DE)

( * ) Notice: Subject to any disclaimer, the term of this patent is extended or adjusted under 35 U.S.C. 154(b) by 408 days.

(21) Appl. No.: 10/593,353

(22) PCT Filed: Mar. 16, 2005

(86) PCT No.: PCT/EP2005/002810
§ 371 (c)(1), (2), (4) Date: Jun. 19, 2007

(87) PCT Pub. No.: WO2005/089727
PCT Pub. Date: Sep. 29, 2005

(65) Prior Publication Data
US 2008/0020051 A1  Jan. 24, 2008

(30) Foreign Application Priority Data
Mar. 19, 2004 (DE) .......................... 10 2004 013 637

(51) Int. Cl.
*B32B 5/16* (2006.01)
(52) U.S. Cl. ......... 424/489; 424/490; 427/212; 428/403
(58) Field of Classification Search .................. None
See application file for complete search history.

(56) References Cited

U.S. PATENT DOCUMENTS

| | | | |
|---|---|---|---|
| 3,041,289 A | 6/1962 | Katchen et al. |
| 3,251,800 A | 5/1966 | Colley et al. |
| 3,429,827 A | 2/1969 | Ruus |
| 3,855,172 A | 12/1974 | Iler et al. |
| 4,001,140 A | 1/1977 | Foris et al. |
| 4,087,376 A | 5/1978 | Foris et al. |
| 4,409,331 A | 10/1983 | Lim |
| 4,487,785 A | 12/1984 | Goosen et al. |
| 4,495,288 A | 1/1985 | Jarvis, Jr. et al. |
| 4,663,286 A | 5/1987 | Tsang et al. |
| 4,683,092 A | 7/1987 | Tsang |
| 4,741,872 A | 5/1988 | De Luca |
| 4,835,248 A | 5/1989 | Bader et al. |
| 4,940,588 A | 7/1990 | Sparks |
| 5,091,187 A | 2/1992 | Haynes |
| 5,162,486 A | 11/1992 | Follmann et al. |
| 5,308,701 A | 5/1994 | Cohen et al. |
| 5,344,487 A | 9/1994 | Whalen-Shaw |
| 5,427,767 A | 6/1995 | Kresse et al. |
| 5,487,390 A | 1/1996 | Cohen et al. |
| 5,512,332 A | 4/1996 | Liberti et al. |
| 5,674,519 A | 10/1997 | Curtis et al. |
| 5,705,222 A | 1/1998 | Somasundaran et al. |
| 5,716,709 A | 2/1998 | Ferguson et al. |
| 5,756,210 A | 5/1998 | Dupuis et al. |
| 6,013,284 A | 1/2000 | De Miquel Ignacia et al. |
| 6,017,559 A | 1/2000 | Mulqueen et al. |
| 6,051,372 A | 4/2000 | Bayerl et al. |
| 6,203,909 B1 | 3/2001 | Chassot |
| 6,423,338 B1 | 7/2002 | Larson et al. |
| 6,479,146 B1 | 11/2002 | Caruso et al. |
| 6,689,478 B2 | 2/2004 | Laguitton |
| 6,699,501 B1 | 3/2004 | Neu et al. |
| 6,833,192 B1 | 12/2004 | Caruso et al. |
| 7,101,575 B2 | 9/2006 | Donath et al. |
| 2002/0039648 A1 | 4/2002 | Horpel et al. |
| 2002/0172716 A1* | 11/2002 | Walt et al. .................. 424/491 |
| 2002/0187197 A1 | 12/2002 | Caruso et al. |
| 2004/0013728 A1 | 1/2004 | Voigt et al. |
| 2004/0142341 A1* | 7/2004 | Schmitt et al. .................. 435/6 |
| 2006/0251701 A1 | 11/2006 | Lynn et al. |
| 2006/0275373 A1 | 12/2006 | Donath et al. |
| 2006/0275374 A1 | 12/2006 | Donath et al. |
| 2006/0275375 A1 | 12/2006 | Donath et al. |
| 2007/0020469 A1 | 1/2007 | Wood et al. |

FOREIGN PATENT DOCUMENTS

| | | |
|---|---|---|
| CA | 2012311 | 9/1990 |
| DE | 4312970 | 10/1994 |
| DE | 19812083 A1 | 9/1999 |
| DE | 19907552 A1 | 8/2000 |
| DE | 10031281 A1 | 1/2002 |
| DE | 10121903 A1 | 10/2002 |
| DE | 102004013637 | 3/2004 |
| EP | 0127713 | 12/1984 |
| EP | 0127989 | 12/1984 |
| EP | 0152898 | 8/1985 |

(Continued)

OTHER PUBLICATIONS

Decher and Schlenoff, 2002. Multilayer Thin Films; Chapter 1. Polyelectrolyte Multilayers pp. 87-97; Chapter 8. Layer by Layer Assembly of Nanoparticles and Nanocolloids p; Chapter 12. Coated Colloids: preparation, Characterization, Assembly, and Utilization. pp. 331-362.*

Lars Dähne et al. "Fabrication of Micro Reaction Cages with Tailored Properties." J. Am. Chem. Soc. 2001 vol. 123: pp. 5431-5436.

(Continued)

*Primary Examiner* — Yvonne L Eyler
*Assistant Examiner* — Suzanne Ziska
(74) *Attorney, Agent, or Firm* — Fanelli Haag, PLLC (57) ABSTRACT

A process for the production of CS particles (10) and microcapsules (12) is described, in which at least one active compound (4) is adsorbed in porous templates (2) (A), as a result of which templates (5) filled with active compounds are present. Subsequently, the templates (2) are provided (B) with a primer layer (6) which is intended to facilitate the subsequent construction of the capsule shell (9). The capsule shell is formed (C) by applying alternately charged polyelectrolyte layers (8). Filled CS particles (10) are obtained. By subsequent dissolution of the templates (2) the active compounds (4) are released (D) from the template into the interior of the microcapsules. The active compounds (4) remain enclosed there or are slowly released (E) from the capsule.

21 Claims, 7 Drawing Sheets
(7 of 7 Drawing Sheet(s) Filed in Color)

FOREIGN PATENT DOCUMENTS

| | | |
|---|---|---|
| EP | 0188309 | 7/1986 |
| EP | 0336014 | 10/1989 |
| EP | 0388758 | 9/1990 |
| EP | 0392487 | 10/1990 |
| EP | 0415273 | 3/1991 |
| EP | 0443428 | 8/1991 |
| EP | 0472990 | 3/1992 |
| EP | 0516252 | 12/1992 |
| EP | 540582 | 8/1994 |
| EP | 0667148 | 8/1995 |
| EP | 0823331 | 2/1998 |
| EP | 0972563 A1 | 1/2000 |
| EP | 1116516 | 7/2001 |
| EP | 1867325 | 12/2007 |
| GB | 1183403 | 3/1970 |
| GB | 2135954 | 9/1984 |
| GB | 2145992 | 4/1985 |
| GB | 2153780 | 8/1985 |
| JP | 60-190229 | 9/1985 |
| JP | 62-213839 | 9/1987 |
| JP | 02-001307 | 1/1990 |
| JP | 02-290241 | 11/1990 |
| JP | 03-137152 | 6/1992 |
| JP | 07-213889 | 8/1995 |
| JP | 07-251003 | 10/1995 |
| JP | 08-169982 | 7/1996 |
| JP | 09-012938 | 1/1997 |
| JP | 09-077605 | 3/1997 |
| JP | 09-208440 | 8/1997 |
| WO | WO 92/00998 | 1/1992 |
| WO | WO 92/05778 | 4/1992 |
| WO | WO 95/26714 | 10/1995 |
| WO | WO 96/02136 | 2/1996 |
| WO | WO 96/18498 | 6/1996 |
| WO | WO 96/30409 | 10/1996 |
| WO | WO 98/14180 | 4/1998 |
| WO | WO 98/47948 | 10/1998 |
| WO | WO99/47252 A | 9/1999 |
| WO | WO 00/03797 | 1/2000 |
| WO | WO01/51196 A | 7/2001 |
| WO | WO 01/64330 | 9/2001 |
| WO | WO03/090920 A | 11/2003 |
| WO | WO 2004/030648 | 4/2004 |
| WO | WO 2004/030649 | 4/2004 |
| WO | 2005032512 A2 | 4/2005 |
| WO | WO 2005/089825 | 9/2005 |

OTHER PUBLICATIONS

Igor L. Radtchenko et al. "Incorporation of macromolecules into polyelectrolyte micro- and nanocapsules via surface controlled precipitation on colloidal particles." Colloids and Surfaces A: Physicochemical and Engineering Aspects. 2002 vol. 202: pp. 127-133.

Dmitry V. Volodkin et al. "Matrix Polyelectrolyte Microcapsules: New System for Macromolecule Encapsulation." Langmuir. 2004 vol. 20(8): pp. 3398-3406.

Lars Dähne et al. "Nanoengineered Capsules with Specific Layer Structures." Encyclopedia of Nanoscience and Nanotechnology. Marcel Dekkar, Inc. 2004: pp. 2355-2367.

Edwin Donath et al. "Novel Hollow Polymer Shells by Colloid-Templated Assembly of Polyelectrolytes." Angew. Chem. Int. Ed. 1998 vol. 37(16): pp. 2201-2205.

Alexei A. Antipov et al. "Polyelectrolyte multilayer capsule permeability control." Colloids and Surfaces A: Physicochemical and Engineering Aspects. 2002 vols. 198-200: pp. 535-541.

H. Möhwald et al. "Smart Capsules." Multilayer Thin Films. Ed.: J. B. Schlenoff. New York 2003: pp. 363-392.

Dmitry G. Shchukin et al. "Smart Inorganic/Organic Nanocomposite Hollow Microcapsules." Angew. Chem. Int. Ed. 2003 vol. 42: pp. 4472-4475.

Gemma Ibarz et al. "Smart Micro- and Nanocontainers for Storage, Transport, and Release." Adv. Mater. 2001 vol. 13(17): pp. 1324-1327.

International Search Report, PCT/EP/2005/002810, Aug. 23, 2005.

Wang, D. and Caruso, F., "Polyelectrolyte-Coated Colloid Spheres as Templates for Sol-Gel Reactions," Chem. Mater., vol. 14, 2002, pp. 1909-1913, XP002339641.

German Office Action dated Mar. 26, 2009. Considered only partial translation below.

English Translation in Part of German Office Action dated Mar. 26, 2009. Considered only translation in part of German OA.

Sukhorukov, et al., "Stepwise Polyelectrolyte Assembly on Particle Surfaces: A Novel Approach to Colloid Design", Polym. Adv. Technol. 9, (1998) pp. 759-767.

Sukhorukov, et al., "Layer-By-Layer Self Assembly of Polyelectrolytes on Colloidal Particles", Colloids and Surfaces, 137 (1998) pp. 253-266.

Donath, et al., "Nonlinear Hairy Layer Theory of Electrophoretic Fingerprinting Applied to Consecutive Layer by Layer Polyelectrolyte Adsorption onto Charged Polystyrene Latex Particles", Langmiur 1997, vol. 13, pp. 5294-5305.

Caruso, et al., "Influence of Polyelectrolyte Multilayer Coatings on Föerster Resonance Energy Transfer Between 6-Carboxyfluorescein and Rhodamine B-Labeled Particles in Aqueous Solution", J. Phys. Chem., 1999, vol. 102, pp. 2011-2016.

Wang, et al., "Polyelectrolyte-Coated Colloid Spheres as Templates for Sol-Gel Reactions", Chem Mater., 2002, vol. 14, 1909-1913.

Written Opinion of the International Searching Authority for International Application No. PCT/EP2008/057434, Nov. 26, 2009.

A.S. Michaels, "Polyelectrolyte Complexes", J. Indust. & Eng. Otem., Oct. 1965, 57(10), 1965, pp. 32-40.

Petrak K., "Review: Polyelectrolyte Complexes in Biomedical Application", J. Bioactive & Compatible Biopolymers, 1986, vol. 1, pp. 202-219.

Johansen, et al., "Bnmobilization of Yeast Cells Binternal Gelation of Alignate", Enzyme Microb. Technol., 1987. vol. 8, pp. 145-148.

C.A. Finch, "Polymers for Microcapsule Walls", Chemistry and Industry, 1985, pp. 752-756.

Encyclopedia of Chemical Technology "Microencapsulation", 1981, vol. 15, Third Edition, pp. 1A-25A.

C.E. Camp, et al., "Calcium Alginate-Immobilized Hepatic Microsomes: Effect of NADPH Cofactor on Oxidation Rates", Enzyme Micro. Technol., 1987, vol. 9, pp. 685-689.

Donath, et al., "Novel Hollow Polymer Shells by Colloid-Templated Assembly of Polyelectrolytes", Angew. Chem. Int. Ed., 1998, vol. 37, No. 16, pp. 2202-2205.

Kim, et al., "Effect of Organic Solvent on the Permeability and Stiffness of Polyelectrolyte Multilayer Microcapsules", Macromolecules, 2005, vol. 38, pp. 5214-5222.

Decher G., et al., "Buildup of Ultrathin Multilayer Films by a Self-Assembly Process: Ill. Consecutively Alternating Adsorption of Anionic and Cationic Polyelectrolytes on Charged Surfaces", Thin Solid Films, 1992, vol. 210-211, No. 1-2, Part 2, pp. 831-835.

Meldrum, et al., "Magnetoferritin: In Vitro Synthesis of a Novel Magnetic Protein", Science, 1992, vol. 257, pp. 522-523.

Caruso, et al., "Investigation of Electrostatic Interactions in Polyelectrolyte Multilayer Films: Binding of Anionic Fluorescent Probes to Layers Assembled onto Colloids", Macromolecules, 1999, vol. 32, pp. 2317-2328.

Kawahashi, et al., "Preparation and Properties of Uniform Coated Colloidal Particles", Journal of Colloid and Interface Science, 1990, vol. 138, No. 2,pp. 534-542.

Philipse et al., "Magnetic Silica Dispersions: Preparation and Stability of Surface-Modified Silica Particles with a Magnetic Core", Langmuir, 1994, vol. 10, pp. 92-99.

* cited by examiner

METHOD FOR PRODUCING CORE-SHELL (CS) PARTICLES AND MICROCAPSULES USING POROUS TEMPLATES, CS PARTICLES AND MICROCAPSULES, AND THE USE THEREOF

The invention is in the field of colloid technology and relates to a process for the production of CS particles and filled microcapsules using porous templates, and to CS particles and microcapsules.

Microcapsules formed of alternately adsorbed poly-electrolyte layers (Layer by Layer, LbL) are known, for example, from [1] and described in DE 198 12 083 A1, DE 199 07 552 A1, EP 0 972 563 A1, WO 99/47252 and U.S. Pat. No. 6,479,146, the disclosure contents of which are hereby completely included. On account of their adjustable semipermeability, such capsule systems have a high application potential as microreactors, drug delivery systems etc. The prerequisite is filling with appropriate active compounds, enzymes, polymers or catalysts.

Furthermore, separating membranes of composite materials which are substance-permeable and coated with polyelectrolyte layers are known from DE 100 31 281 A1.

Hitherto, LbL microcapsules were mainly produced which in the interior contain the same medium (solvent) as outside. In most applications, however, functionalized macromolecules are needed in the interior which should be permanently immobilized and present in dissolved form there in order to maintain their functionality. The known processes for the production of such filled capsules can only be employed under certain conditions. Especially for sensitive biomolecules, difficulties occur with filling according to the known methods.

Hitherto, 4 possibilities for filling with macromolecules have been developed.

a) Ship in bottle synthesis[2]

Monomers are polymerized in the presence of capsules. The small initiator and monomer molecules penetrate into the capsules. After the polymerization, the polymers synthesized in the solution are washed away, while the polymers formed in the interior of the capsules can no longer diffuse through the capsule wall and are immobilized in the interior. This method, however, is restricted to synthetic molecules.

b) Switching of the permeability[3,4]

Here, capsules are used whose permeability changes with change in the pH or the ionic strength of the solution. The capsules are added to a solution of the macromolecule and switched into a permeable state by addition of salt or change in the pH. After the penetration of the polymers, the pH is switched back again or the salt is washed away and the macromolecules are immobilized in the interior. The disadvantage lies in the necessity of using special, switchable capsules. Furthermore, hitherto only low concentrations can be encapsulated.

c) Controlled precipitation[5]

In this method, the filling is precipitated before the application of the LbL shell to the template. For this purpose, either a low solubility in a specific solvent or a complexation of the macromolecule with an auxiliary is utilized. Subsequently, a standard LbL coating is applied to the precipitate layer. The template is dissolved. By change of the solubility or the decomposition of the complex, the macromolecule is dissolved from the interior surface of the capsules into the capsule interior. This method must be very specifically optimized for each filling material, which has hitherto succeeded only on selected examples. Frequently, the precipitate layers are not homogeneous enough (rough surface) in order to apply a well-defined LbL capsule. Furthermore, in the case of biopolymers the dissolution of the template must be carried out under mild conditions, which is not the case with the melamine-formaldehyde (pH 1), erythrocyte (pH 12, NaOCl) and polystyrene particles (tetrahydrofuran) usually used.

d) Porous $CaCO_3$ Templates[9]

In this approach, porous $CaCO_3$ templates are used. The templates are suspended in solutions of alternately charged polyelectrolytes. In this process, the outer and the inner surface of the porous templates is coated with polyelectrolytes. After dissolving the $CaCO_3$ template using EDTA, microcapsules having an inner framework of polyelectrolytes remain, which is surrounded by a polyelectrolyte shell which is not closed. Subsequently, macro-molecules can then add to the inner framework of the microcapsules. Using this process, closed capsule shells cannot be produced, since the pores of the $CaCO_3$ templates are relatively large.

It is therefore the object of the present invention to provide a process for encapsulating materials or active compounds in which the active compounds to be encapsulated can be enriched simply and in high concentrations in the interior of the capsules.

According to the invention, this object is achieved by a process for the production of CS particles and/or microparticles having the steps:

at least one active compound to be encapsulated is adsorbed in porous templates;

a capsule shell is formed around the porous templates by applying alternately charged polyelectrolyte and/or nanoparticle layers.

As a result, initially CS particles are formed which still contain the porous template as a core containing the adsorbed active compound. Subsequently, the porous template can be dissolved out of the CS particles, microcapsules being formed which are filled with the active compound. Before formation of the capsule shells, at least one primer layer can be applied to the porous templates. If appropriate, further additional layers of polyelectrolytes and/or nanoparticles are applied to the primer layer before the formation of the actual capsule shell. Typically, the capsule shells are prepared by sequential adsorption of alternately charged polyelectrolytes ("LbL process"). Typically, many templates prepared as a colloidal solution are simultaneously coated so that each template is provided with a capsule shell. In consequence, a colloidal solution of CS particles or, after dissolution of the templates, a colloidal solution of microcapsules is obtained, which can optionally be further treated.

In the context of the present invention, porous templates are understood as meaning those particles which have a large number of pores or internal cavities. After the application of the LbL layers and, if appropriate, of a primer layer to the porous templates, core-shell (CS) particles are obtained, which are designated as CS particles. After dissolving out the original porous template, only the shell still exists, i.e. the capsule shell, if appropriate with an internal primer layer, which in the simplest case is filled with the external solvent or with a solution or suspension of the included active compound. These filled shells are designated as capsules or microcapsules. The CS particles or microcapsules are filled with the active compound, i.e. the active compound remains in the CS particles or microcapsules, since the capsule shell acts as a diffusion barrier with respect to the active compound. Colloidal particles which are used for filling the porous particles or for the construction of the LbL shell, and therefore are in general smaller than 100 nm, are designated as nanoparticles.

In contrast to the known methods, the invention described here offers a novel, simple and general method for the encapsulation of materials even in high concentration in CS particles and microcapsules (Layer by Layer polyelectrolyte capsules). LbL CS particles and microcapsules filled with active compounds are produced here with the aid of porous templates. For this, the porous templates are filled with one or more active compounds before LbL coating. If the active compound is only adsorbed inadequately in the pores, special auxiliaries (mediators) or pH changes can be utilized to improve the filling. The filled templates are covered with a special primer which does not penetrate into the pores, but seals it for subsequent coatings. Afterward, the construction of the capsule shell or wall takes place by means of alternating adsorption of polycations and polyanions, whereby a filled CS particle results. For the production of microcapsules, the porous templates can be removed using solvents. Especially in the case of silica particles ($SiO_2$), this can be carried out under mild conditions above pH 4, in order to spare, for example, biological active compounds.

The templates used are porous microparticles whose size is preferably less than 100 μm. The microparticles contain pores having, for example, a pore width of 0.3 nm-100 nm, preferably of 1 nm-30 nm and particularly preferably of 6 nm-10 nm. In many applications, the lower limit of the pore width can be between 1 nm and 6 nm, for example 2 nm or 4 nm, and the upper limit of the pore width can be between 10 nm and 40 nm, for example 15 nm or 30 nm. In principle, the pore width should be so large that the active compounds to be encapsulated penetrate into the pores and can be deposited in the pores, i.e. in particular adsorb in the interior of the pores. Porous templates having a large interior surface are therefore preferred, the interior surface being formed from the inner walls of the pores. In particular, the inner surface effectively available for the adsorption of the active compounds should be large. Effective interior surface is understood here as meaning the part of the surface which is actually available for the adsorption of an active compound of specific size. Since the templates frequently contain pores having different width, large molecular weight active compounds can only penetrate into suitably large pores whereas for smaller molecules the smaller pores are also available. Therefore, the pore size can also be described by means of the size of the nanoparticles or molecules or their molecular weight, which can still penetrate into the pores. The lower limit of the molecular weight is preferably 100 g/mol. The upper limit corresponds to a molecular weight of approximately $5\times10^6$ g/mol. In this process, the shape of the penetrating molecule (linear or globular) also plays an important role.

It is furthermore possible for the surface of the pore cavities to be coated by a number of layers of alternately charged polyelectrolytes and/or nanoparticles preferably using the LbL technique, i.e. polyelectrolyte and/or nanoparticle layers are formed on the "interior" surface of the porous templates. The size of the nanoparticles or the molecular weight of the polyelectrolytes is appropriately matched to the pore width. After the dissolution of the templates, a filigree negative impression of the original pore structure of insoluble complexes of polyelectrolyte complexes and/or polyelectrolyte/nanoparticle complexes (interior framework) is obtained which mechanically stabilizes the capsules and greatly increases their interior surface. The active compound to be encapsulated is in this case the material of the interior framework. Additionally, before coating or after the dissolution of the porous template, a further active compound can be intercalated and/or deposited on the interior framework (e.g. by precipitation and/or adsorption), which is then bonded, for example, to the interior framework. In addition to the mechanical stabilization, the advantage of an interior framework is a marked increase in the interior surface of the microcapsules.

Furthermore, the object is achieved by CS particles having
  a diameter of less than 100 μm;
  a porous core in which at least one active compound is adsorbed; and
  a capsule shell of a number of layers of alternately charged polyelectrolyte and/or nanoparticle layers.

The porous core is the porous templates described. Optionally, between the porous core and the capsule shell can be arranged a primer layer, which surrounds the core and contributes to the improvement of the construction of the capsule shell.

Furthermore, the object is achieved by microcapsules having
  a diameter of less than 100 μm;
  a capsule shell of a number of layers of alternately charged polyelectrolyte and/or nanoparticle layers,
  a primer layer on the inside of the capsule shell; and
  at least one active compound which is enclosed in the interior of the microcapsules.

In these microcapsules, the porous template or the porous core is removed.

It is further within the scope of the invention to produce microtemplates using the following steps:
  at least one porous template is prepared;
  the surface of the pore cavities of the porous template is coated with a number of layers of alternately charged polyelectrolytes and/or nanoparticles; and
  the porous template is dissolved, a micro-template consisting of the polyelectrolyte and/or nanoparticle layers remaining.

The polyelectrolyte and/or nanoparticle layers can optionally be additionally crosslinked (e.g. covalently) before or after the dissolution of the template in order to increase the stability of the microtemplate. In consequence, a filigree framework is again present that corresponds largely to a negative impression of the interior pore structure of the template and here represents the microtemplate. In the coating of the pore surface, it can, of course, also occur that on the outside of the template polyelectrolyte and/or nanoparticle layers are formed which also remain after the dissolution of the template. Depending on the size of the polyelectrolytes and/or nanoparticles used, the shell thus formed is only partly or alternatively to a large extent completely constructed. The microtemplates formed can now be the starting point for the production of further microparticles, e.g. active compounds can be deposited on the framework. The microtemplates are distinguished by a relatively large surface together with a small volume and therefore offer many binding sites for active compounds to be deposited. In comparison to the microcapsules having an interior framework, in the case of the microtemplates no capsule shell having an optional primer layer is formed after the filling of the template with polyelectrolyte and/or nanoparticle layers. The production of the microtemplates and the microcapsules having an internal framework, however, can be carried out using identical materials and under identical conditions. The size of the microtemplates corresponds to the size of the templates used and is therefore in the range indicated above.

The CS particles and/or microcapsules produced and filled with the active compound can be advantageously used in many fields, for example

- for the encapsulation of substances in the fields of diagnosis, sensors; and/or
- for the selective accumulation of substances from solutions for applications in water purification, diagnostics, nuclear chemistry etc.; and/or
- for the inclusion of substances having catalytic action, in particular metals and/or metal oxides and/or enzymes, for the catalysis of chemical and biochemical reactions; and/or
- for the encapsulation of nanoparticles, in particular for the production of fluorescent or magnetic microcapsules, for diagnostic or medical applications; and/or
- for the encapsulation and release of active compounds in the pharmaceutical and cosmetics industry; and/or
- for separation purposes, e.g. in chromatography; and/or
- for applications in the foodstuffs industry and agriculture and forestry.

Further advantageous embodiments of the invention, independently of whether the process, the CS particles or microcapsules are concerned, are described below with the aid of the figures. In these.

The patent or application file contains at least one drawing executed in color. Copies of this patent or patent application publication with color drawing(s) will be provided by the Office upon request and payment of the necessary fee.

Figure 1A:
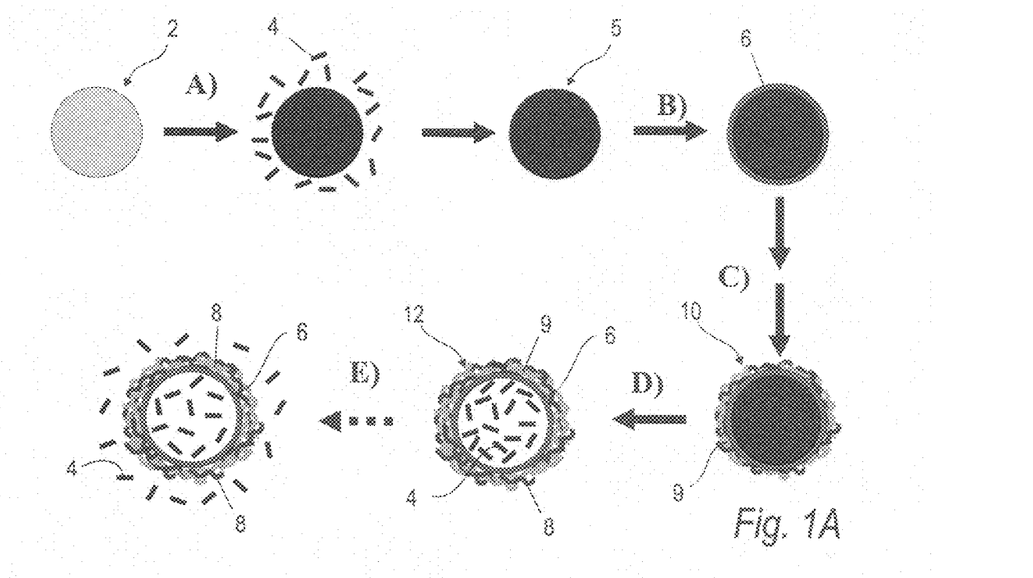
FIG. 1 shows individual process steps of the process according to the invention and the CS particles or microcapsules obtained in this process.
Figure 1B:
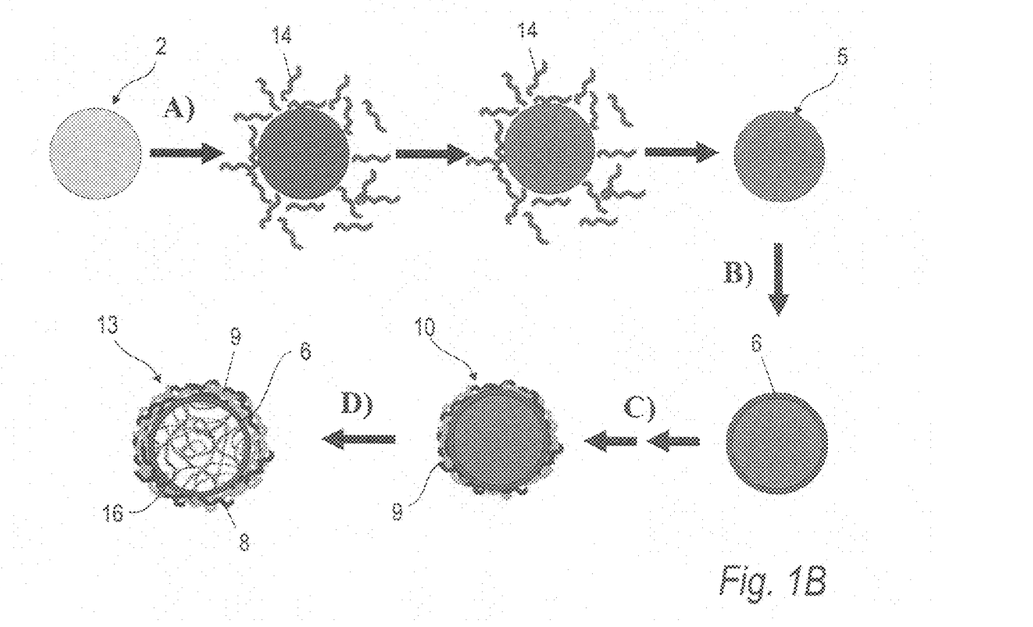

The individual process steps are illustrated with the aid of FIG. 1. Preferably, colloidal particles (templates) having a defined porosity are used, which can be filled with the materials to be encapsulated (called active compound below) in the desired concentration. FIG. 1A shows filling with an active compound which at a later point in time is immobilized permanently in the interior or in the case of appropriate wall permeability is released in metered form. In comparison, the formation of a microcapsule having an internal framework is shown in FIG. 1B.

The active compound can be any material which
1. can accumulate in the interior of porous templates and
2. can be retained for a specified period by means of an LbL shell.

The active compounds can be present in molecular form, aggregated, as a complex or in colloidal form. In particular, the active compounds to be encapsulated are polymers and/or proteins and/or organic molecules having molecular weights over 100 g/mol and/or nanoparticles. In particular, they can in this case be enzymes and/or catalysts and/or dyes and/or pharma-ceutical or cosmetic active compounds and/or plant protection agents. The active compounds to be encapsulated can have a different affinity or binding constant with respect to deposition in the pores. The active compounds occupy the available binding sites on the interior surface depending on their binding constants. This different affinity can be utilized in the loading of the templates with a number of active compounds.

Porous templates 2 are colloidal inorganic and organic particles in the size range suitable for LbL capsules between 100 nm and 100 µm, in particular between 500 nm and 15 µm or 30 µm. A distribution of the pore size of these templates 2 which is as small as possible is preferred here, i.e. the pores should preferably largely have the same pore width. In particular, porous colloidal silica particles and/or zeolites and/or organic polymer particles are suitable as templates, since these particles can be produced with a sufficiently narrow distribution of the pore width. Porous zeolite particles in this case have a pore width of, in particular, 0.3 nm to 10 nm.

Filling of the Templates (Step A)

The filling of the porous templates 2 with one or more active compounds 4 can be mediated by attractive interaction, for example take place by adsorption of the active compounds and templates 2 present in a solution (for example an aqueous medium) by means of electrostatic and/or H bonds and/or specific interactions and/or van der Waals interactions. The active compounds used can be organic or inorganic materials, for which Layer by Layer films are impermeable or not very permeable. These materials can be present dissolved, as a solid framework or in colloidal form as nanoparticles. Electrostatic interactions are particularly suitable for the adsorption in the porous templates, since charged materials also form a good exterior surface for the subsequent LbL coating steps. While the filling with molecules which are oppositely charged to the pore or template surface causes no difficulties, materials having an identical charge require special treatment. The three variants mentioned below are in particular suitable therefor:

1. By means of the shift in the pH, the charge of the active compounds themselves or the surface of the template is reversed. As a result, an attractive interaction occurs. Biopolymers having an isoelectric point can thus in particular be adsorbed relatively simply in the templates.
2. The adsorption of the active compounds is mediated by means of suitable auxiliaries (mediators). The auxiliaries can, for example, reverse the charge of the surface of the pores or alternatively make possible specific interactions between the active compounds (e.g. proteins, peptides, further active compounds) and the pore surface. The use of auxiliaries in particular allows a reversal of the charge of surfaces with subsequent adsorption of the identically charged active compounds. Such auxiliaries can be materials which are multiply charged, in particular 2-5 times (e.g. metal$^{3+}$ or polyamines $(NR_4^+)_n$ where n=2-5 or $SO_4^{2-}$, $PO_4^{3-}$, R—$(COO^-)_n$ where n=2-5) which under certain conditions (i.e. at certain pHs and/or ionic strengths) form a complex with the material to be adsorbed and under other conditions (i.e. other pHs and/or ionic strengths) can be removed again.[5]
3. Auxiliaries can also be macromolecules 14 (FIG. 1B) having a charge number n>5, which remain in the microcapsules as dissolved molecules or solid framework structures after the cores have been dissolved out. For the preparation of solid framework structures, LbL structures are produced in the pores by alternating adsorption of comparatively low molecular weight polyelectrolytes. The structures formed correspond to a negative impression of the pores present and can in general subsequently no longer dissolve. After dissolving out of the original template, they remain in the interior of the microcapsules as a filigree network or internal framework 16 (FIG. 1B) having a very large surface. Such structures can be used for the mechanical stabilization of microcapsules or serve for the accumulation of other materials or for catalyst applications due to the large surface.

If a number of active compounds are to be encapsulated, their adsorption can be carried out successively or simultaneously. For filling with the active compounds, pore sizes are used which are related to the size of the molecules to be filled. In particular in the case of silica particles, molecules between 0.1 and 5000 kDa (100 g/mol-5 000 000 g/mol) can be intercalated in pore sizes of 4 to 30 nm. A number of active compounds with comparable binding constants can also be intercalated simultaneously or, in the case of different binding constants, sequentially. Here, the active compound with the higher binding constant is insufficiently filled, i.e. its concentration is chosen such that this active compound does not occupy all available binding sites. Afterward, the incompletely filled particles are filled with the 2nd active compound in a solution by adsorption. In consequence, the templates 4 are largely filled with the active compound(s) 4.

Priming (Step B)

A primer layer 6 of, for example, a polyelectrolyte or of nanoparticles is optionally applied to the now-filled templates 5. The primer material is to be chosen and matched such that it 1. does not penetrate itself into the filled pores,
2. prevents a penetration into the interior of the materials used in the subsequent construction of the LbL capsule shell High molecular weight or/and branched poly-electrolytes and nanoparticles which are matched to the size of the pores are particularly suitable. The primer material 6 typically differs from the materials of the shell to be applied subsequently. If appropriate, it can also be a polyelectrolyte which, however, has a higher molecular weight and/or a more branched structure and/or a better crosslinkage than the LbL capsule shell materials. For this purpose, an extra crosslinking step can be carried out, for example by means of glutaraldehyde in the case of amino-functionalized polyelectrolytes.

Coating (Step C)

Subsequently, alternating layers 8 of cationically and anionically charged substances (polyelectrolytes), preferably polymers, are applied to this primer layer 6 until the desired semi- or impermeability of the LbL capsule wall 9 is achieved for the substance enclosed. The permeability of the LbL capsules can be specifically adjusted here for the particular material encapsulated by means of the layer number, the choice of material, by an aftertreatment by means of annealing, or by implementation of further substances into the capsule wall[8]. After the construction of the capsule wall, CS particles 10 having a filled porous core are present. Suitable substances for the formation of the capsule wall and suitable process courses can be inferred from the already mentioned documents DE 198 12 083 A1, DE 199 07 552 A1, EP 0 972 563 A1, WO 99/47252 and U.S. Pat. No. 6,479,146.

Dissolution of the Cores (Step D)

A subsequent optional dissolution of the cores (templates) out of the CS particles 10 is carried out using a suitable solvent. The products of the dissolution are removed from the capsule interiors by washing with the solvent and water, the filled active compound 4 of greater molecular weight remaining in the interior. In the case of the organic templates, solvents can be organic liquids such as, for example, tetrahydrofuran in the case of polystyrene, or acidic or basic aqueous solutions, such as, for example, HCl in the case of melamine-formaldehyde resins[6]. Silica particles, in particular, can be readily dissolved using 1 mol/l of HF, since the resulting products ($SiF_6^{2-}$) readily diffuse outward through the capsule membrane without damaging the capsule wall.[7] 1 molar HF, however, is not unproblematical for many materials.

Therefore, in particular for sensitive active compounds or sensitive capsule wall materials, gentle dissolution of the silica templates at pH values of 3-6.5 is preferred. Here, a fluoride salt having a concentration of 1-5 mol/l is adjusted to a desired pH of 3-6 using a buffer solution of 1-5 mol/l. Porous silica templates, in particular, dissolve in this reaction mixture without residue with sufficient reaction time. The hexafluorosilicate anions also diffuse out of the capsules without problem through thick LbL layers. The preferred pH range extends from 3 or 3.5 (lower limit) up to 6 or 6.5.

The method described for dissolving the templates can be used independently of whether porous or nonporous microparticles are concerned and is suitable, in particular, for dissolving porous and nonporous silica and zeolite particles. This method is moreover suitable in principle for dissolving such materials, these materials being dissolved in the pH range from 3.5 to 6 by fluoride salts in the presence of buffer solution, in particular of an acetate/acetic acid buffer. This dissolution method is particularly suitable for acid-sensitive materials, which either form the capsule wall or are included in the interior. This relates to many biopolymers such as, for example, proteins, enzymes, DNA, but also acid-sensitive polymers or nanoparticles, such as, for example, magnetite or quantum dots (fluorescent nanoparticles).

Optional Release of the Active Compound (Step E)

After the removal of the template, microcapsules 12 (FIG. 1A) filled with an active compound or microcapsules 13 provided with an inner framework 16 are present. Depending on the permeability of the capsule wall set and the size of the included active compounds, the active compounds remain permanently immobilized in the interior of the microcapsules or are released within a defined period of time.

EXAMPLES

1. Positively Charged Polymer 10 mg of spherical, porous silica templates having a diameter of 10 μm and a pore size of 7 nm are suspended in 100 μl of water (pH 6.5). 500 μl of a solution of 1 g/l of rhodamine-labeled polyallylamine (PAH-Rho; PAH=poly(allylamine hydrochloride)) having a molecular weight of 70 000 g/mol are added thereto and the mixture is incubated for 12 h. The supernatant is washed away with buffer solution. A solution of fluorescein-labeled chitosan (chitosan-Flu) having a molecular weight of >300 000 g/mol in 0.5 mol/l NaCl is then added to the templates and adsorbed on the surface. As the confocal exposure shows, it forms a homogeneous layer on the surface and barely penetrates into the templates (FIG. 2b). After priming, 7 layers of PSS (poly(sodium 4-styrenesulfonate)) and PAH are applied in an alternating manner using solutions of 1 g/l of polymer in 0.5 mol/l of salt. Between the coating steps, washing with water is carried out 3 times. An analysis of the CS particles obtained showed a concentration of 7 g/l of PAH/Rho in the interior (FIG. 2a).

The concentrations of the active compounds in the interior of the CS particles/capsules were determined by means of fluorescence using confocal microscopy with the aid of comparison solutions. In this process, the high concentration of dye in the interior of the capsules can lead to self-quenching, which simulates lower concentrations.

The CS particles were incubated with 100 ml of a solution of 2 mol/l of sodium fluoride in 1 mol/l of acetate buffer (pH 4). After 3 h, the templates (cores) have completely dissolved and the capsules filled with PAH remain (FIG. 2c). After a number of washing cycles with water, a concentration of 6.3 g/l of PAH/Rho was determined in the interior of the capsules, which no longer changed on storage for a number of weeks.

Figure 2:
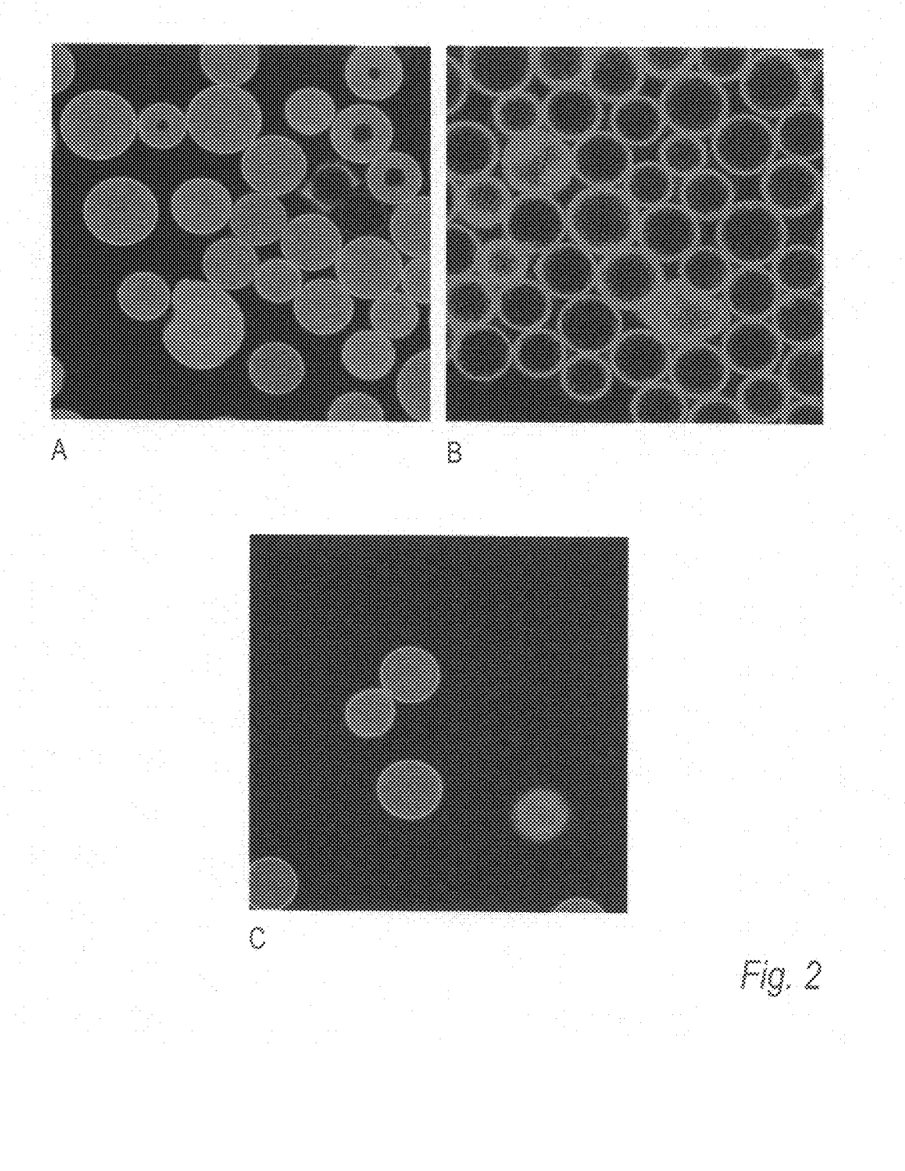
FIG. 2 shows a) and b) CS particles and c) microcapsules containing an encapsulated positive polymer.

FIG. 2 shows CS particles and capsules produced using positively charged polymer in the interior; a) confocal image of CS particles filled with PAH/Rho, which are primed with chitosan-Flu and coated with 7 layers of PAH/PSS (rhodamine channel PMT2 600 V, image size 80 μm×80 μm); b) confocal image of the CS particles (fluorescein channel PMT1 750 V, image size 80 μm×80 μm); c) confocal image of capsules of chitosan (PSS/PAH)$_3$PSS filled with PAH/Rho after dissolving out the SiO$_2$ template (rhodamine channel PMT2 600 V, image size 80 μm×80 μm).

2. Negatively Charged Polymer 10 mg of spherical, porous silica templates having a diameter of 10 μm and a pore size of 7 nm are suspended in 100 μl of water (pH 6.5). Subsequently, the templates are incubated in a 0.1 mol/l solution of FeCl$_3$. After three washing cycles with water, 500 μl of a solution of 1 g/l of rhodamine-labeled polystyrenesulfonate (PSS, MW 130 000 g/mol Capsulation Nanoscience AG) are added and the mixture is incubated for 12 h. The anionically charged PSS-Rho has adsorbed on the surface of the pores via the Fe$^{3+}$. The PSS supernatant is washed away with water. A solution of chitosan-Flu having a molecular weight of >300 000 g/mol in 0.5 mol/l NaCl is then added to the templates and adsorbed on the surface. After priming, 7 layers of PSS and PAH are applied in an alternating manner using solutions of 1 g/l of polymer in 0.5 mol/l of salt. Between the coating steps, washing with water is carried out 3 times. A concentration of 2.3 g/l of PSS-Rho was then determined in the interior of the CS particles thus obtained (FIG. 3a). The concentration of PSS on the wall is particularly high, which is to be attributed to increased adsorption on the interior surface of the chitosan primer. The silica templates are dissolved out using 100 ml of a solution of 2 mol/l of sodium fluoride in 1 mol/l of acetate buffer pH 4. After 3 h, the templates have completely dissolved and the capsules filled with PSS remain (FIG. 3b). A concentration of 1.8 g/l of PSS/Rho was determined in the interior of the capsules, which slightly decreased on storage for a number of weeks.

Figure 3:
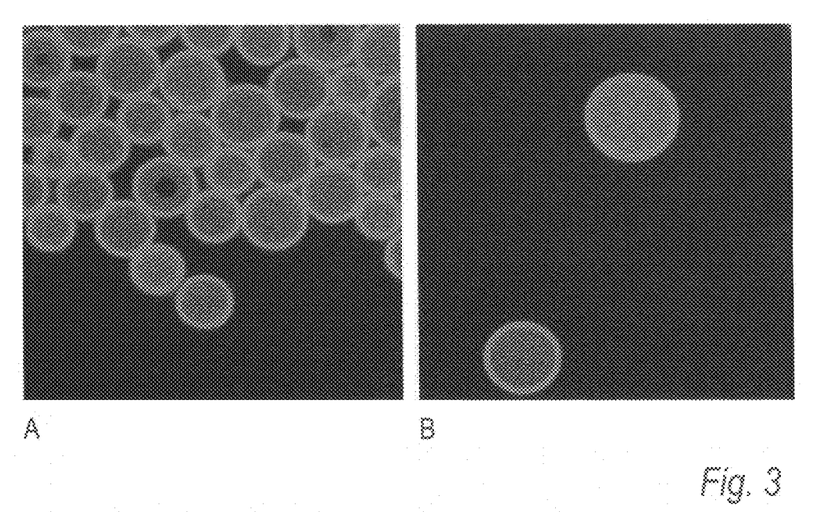
FIG. 3 shows a) CS particles and b) microcapsules containing an encapsulated negative polymer.

FIG. 3 shows capsules produced using negatively charged polymer in the interior; a) confocal image of CS particles filled with PSS/Rho, which are chitosan(PSS/PAH)$_3$PSS-coated (rhodamine channel PMT2 800 V, image size 80 μm×80 μm); b) confocal image of capsules of chitosan(PSS/PAH)$_3$PSS filled with PSS-Rho after dissolving out the SiO$_2$ template (rhodamine channel PMT2 850 V, image size 80 μm×80 μm).

3. Zwitterionic Protein Albumin 10 mg of spherical, porous silica templates having a diameter of 10 μm and a pore size of 7 nm are suspended in 100 μl of water (pH 6.5). 500 μl of a solution of 1 g/l of rhodamine-labeled bovine serum albumin (TRITC-BSA, Sigma; BSA=bovine serum albumin) in acetate buffer (0.1 M, pH 5) are added thereto and the mixture is incubated for 12 h. The supernatant is washed away with buffer solution, the albumin has markedly accumulated in the interior of the templates. A solution of chitosan-Flu having a molecular weight of >300 000 g/mol in 0.5 mol/l of NaCl is then added to the templates and adsorbed on the surface. After priming, 7 layers of PSS and PAH are applied in an alternating manner using solutions of 1 g/l of polymer in 0.5 mol/l of salt. Between the coating steps, washing with water is carried out 3 times. A concentration of 1.2 g/l of BSA was determined in the interior of the CS particles obtained (FIG. 4a). The silica templates were dissolved out in 100 ml of a solution of 2 mol/l of sodium fluoride in 1 mol/l of acetate buffer at a pH of 5. After 12 h, the templates have completely dissolved and the capsules filled with albumin remain (FIG. 4b). In the interior of the capsules, a concentration of 1.4 g/l of BSA was determined, which did not change on storage for a number of weeks. The higher value in the capsules in comparison to the CS particles results either from a decrease in the self-quenching mentioned in the first example or from a detachment of the BSA from the wall in the interior.

Figure 4:
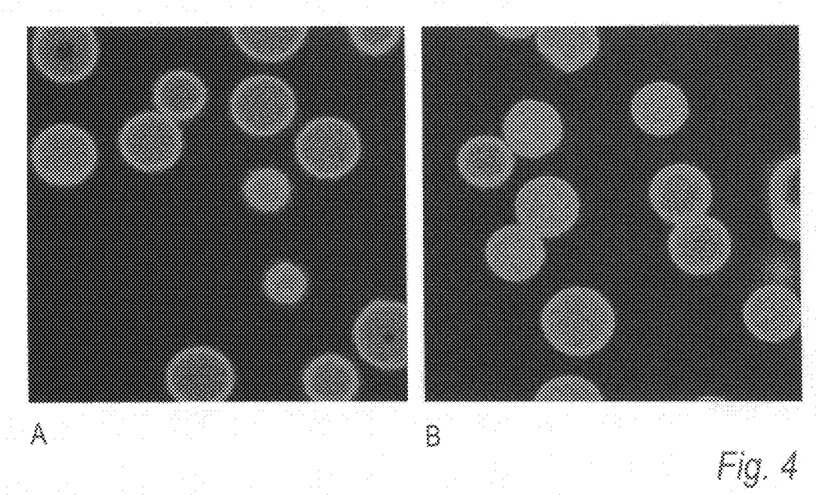
FIG. 4 shows a) CS particles and b) microcapsules containing an encapsulated zwitterionic protein.

FIG. 4 shows capsules produced with proteins in the interior; a) confocal image of CS particles filled with BSA/Rho (BSA labeled with rhodamine), which are coated with chitosan(PSS/PAH)$_3$PSS (rhodamine channel PMT 850 V, image size 80 μm×80 μm); b) confocal image of capsules of chitosan (PSS/PAH)$_3$PSS filled with BSA-Rho after the dissolving out of the SiO$_2$ template (rhodamine channel PMT 900 V, image size 80 μm×80 μm).

4. Sequential Intercalation of 2 Different Active Compounds 10 mg of spherical, porous silica templates having a diameter of 10 μm and a pore size of 7 nm are suspended in 100 μl of water (pH 6.5). 100 μl of a solution of 1 g/l of polyallylamine (PAH) labeled with rhodamine and having a molecular weight of 70 000 g/mol are added thereto and the mixture is incubated for 12 h. The cationically charged PAH/Rho has accumulated in the interior of the particles. PAH is no longer found in the supernatant. In the next step, a solution of 500 μl of fluorescein-labeled chitosan having a molecular weight of 50 000-300 000 g/mol is added to the particles and the mixture is incubated for a further 12 h. After washing away the chitosan supernatant, a solution of chitosan having a molecular weight of >300 000 g/mol in 0.5 mol/l of NaCl is added to the particles and adsorbed on the surface. After priming, 7 layers of PSS and PAH are applied alternately using solutions of 1 g/l of polymer in 0.5 mol/l of salt. Between the coating steps, washing with water is carried out 3 times. As the confocal exposures show (FIG. 5a,b), 2.5 g/l of PAH/Rho and 7 g/l of low molecular weight chitosan-Flu are found in the interior of the CS particles. The silica templates were dissolved out with 100 ml of a solution of 2 mol/l of sodium fluoride in 1 mol/l of acetate buffer pH 4. After 3 h, the templates have completely dissolved and the capsules filled with PAH and chitosan remain (FIG. 5c,d). Concentrations of 1.7 g/l of PAH/Rho and of 7 g/l of chitosan-Flu were determined in the interior of the capsules, which did not change on storage for a number of weeks.

Figure 5:
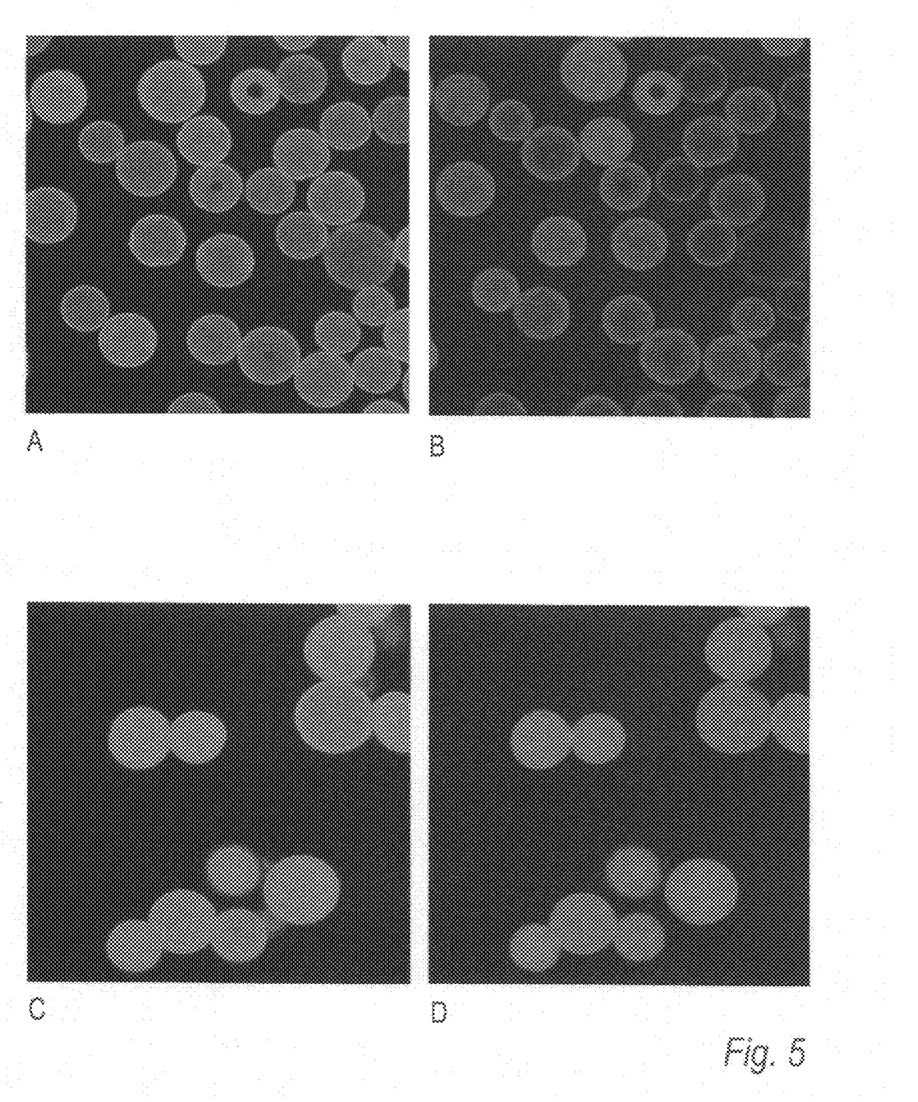
FIG. 5 shows a) and b) CS particles and c) and d) microcapsules containing a number of encapsulated active compounds.

FIG. 5 shows confocal images of CS particles and capsules which are filled with 2 positively charged polymers PAH/Rho and low molecular weight chitosan-Flu and encapsulated using chitosan (PSS/PAH)$_3$PSS; a) CS particles in the rhodamine channel PMT2 600 V, image size 80 μm×80 μm; b) CS particles in the fluorescein channel PMT1 500 V, image size 80 μm×80 μm; c) capsules in the rhodamine channel PMT2 700 V, image size 80 μm×80 μm, d) capsules in the fluorescein channel PMT1 550 V, image size 80 μm×80 μm.

Figure 6:
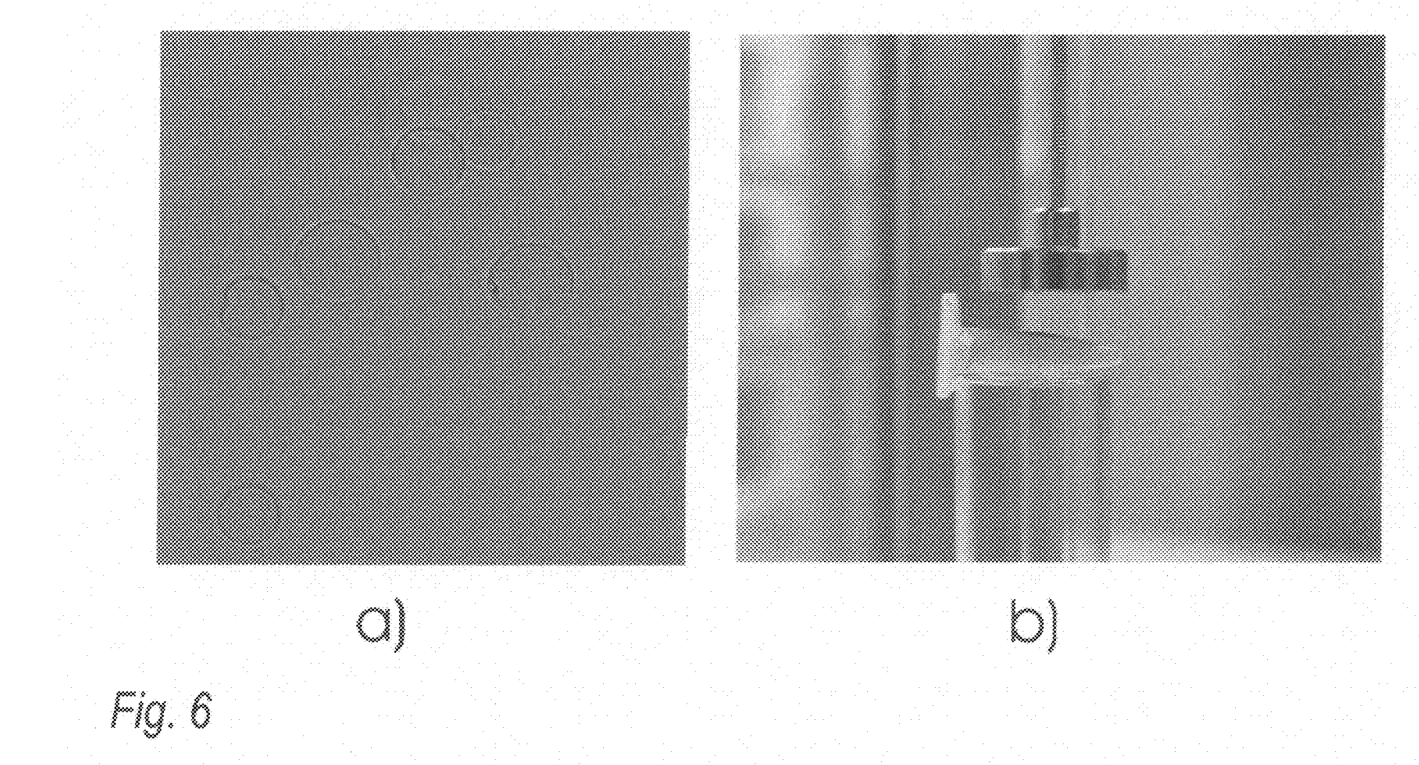
FIG. 6 shows a) capsules filled with nanoparticles b) superparamagnetism in capsules filled with nanoparticles.

5. Filling with Nanoparticles 10 mg of spherical, porous silica templates having a diameter of 10 μm and a pore size of 10 nm are suspended in 100 μl of water (pH 6.5). 100 μl of a solution of 1 g/l of positively charged magnetite nanoparticles having a diameter of 5-10 nm in an acetate buffer solution pH 5.2 are added thereto. After a 12 h incubation, the supernatant is washed away. The porous templates show a marked superparamagnetic activity. A solution of chitosan having a molecular weight of >300 000 g/mol in 0.5 mol/l NaCl is added to the templates and adsorbed on the surface. After priming, 7 layers of PSS and PAH are applied alternately using solutions of 1 g/l of polymer in 0.5 mol/l of salt. Between the coating steps, washing with water is carried out 3 times. After the coating, the magnetic activity has not changed. The silica templates were dissolved out using 100 ml of a solution of 2 mol/l of sodium fluoride in 1 mol/l of acetate buffer pH 4.5. After 12 h, the templates have completely dissolved and the capsules filled with magnetite remain (FIG. 6a). The magnetic activity barely decreased during the dissolution (FIG. 6b).

FIG. 6a shows confocal images of capsules which are filled with positively charged magnetite nanoparticles and encapsulated using chitosan $(PSS/PAH)_3PSS$ (80 μm×80 μm). FIG. 6b shows how the capsules can be collected in an Eppendorf tube by means of a magnet on the top.

6. Microcapsules Having a Solid Structural Framework in the Interior 10 mg of spherical, porous silica templates having a diameter of 10 μm and a pore size of 10 nm are suspended in 100 μl of water (pH 6.5). 100 μl of a solution of 1 g/l of polyallylamine (PAH) labeled with rhodamine and having a molecular weight of 15 000 g/mol in 0.5 mol/l NaCl are added thereto and the mixture is incubated for 60 min with the temporary application of ultrasound. The cationically charged PAH/Rho has accumulated in the interior of the particles. The excess of PAH/Rho is washed away. Afterward, the mixture is incubated with PSS 20 000 g/mol in 0.5 mol/l of salt and the supernatant is washed away. This process is carried out 4 times (8 layers). Afterward, a solution of chitosan having a molecular weight of >300 000 g/mol in 0.5 mol/l of NaCl is added to the particles and adsorbed on the surface. After priming, 7 layers of PSS and PAH 70 000 (labeled with the dye Cy5) are applied alternately using solutions of 1 g/l of polymer in 0.5 mol/l of salt. Between the coating steps, washing with water is carried out. As the confocal exposures show (FIG. 7a,b), PAH/Rho is found in the interior of the CS particles, while the Cy5-labeled PAH forms the shell. 21.5 g/l of PAH/Rho was determined as the concentration. The silica templates were dissolved out using 100 ml of a solution of 2 mol/l of sodium fluoride in 1 mol/l of acetate buffer pH 4. After 3 h, the templates have completely dissolved and the capsules filled with the PSS/PAH-Rho remain (FIG. 7c). Concentrations of 16.9 g/l of PAH/Rho were determined in the interior of the capsules, which are guaranteed to be markedly higher because of the self-quenching occurring in the complex framework. In contrast to the conventional capsules, these capsules do not collapse during drying owing to the stable framework (FIG. 7d,e). Furthermore, the locational stability of the filigree framework in the interior was demonstrated by the bleaching of areas (2 points left and right of the center) and subsequent scanning with the confocal microscope (FIG. 7c).

Figure 7:
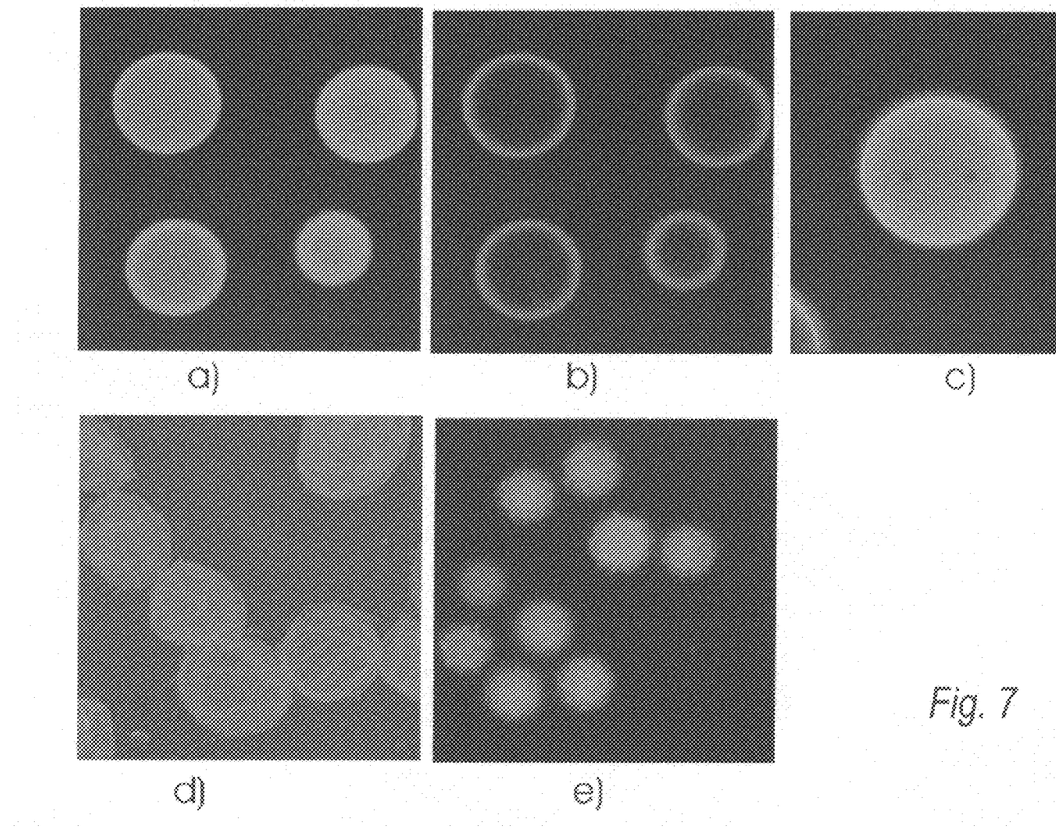
FIG. 7 shows a) and b) CS particles and c) and d) microcapsules filled with a PAH-Rho/PSS complex framework.

FIG. 7 shows confocal images of CS particles and capsules which are filled with a PAH-Rho/PSS complex and surrounded with chitosan $(PSS/PAH)_3PSS$, a) CS particles in the rhodamine channel PMT2 600 V, image size 40 μm×40 μm; b) CS particles in the Cy5 channel PMT1 500 V, image size 40 μm×40 μm; c) capsules in the rhodamine and Cy5 channel superimposed, 2 holes which are location-stable were burnt in the capsules using high laser power, image size 40 μm×40 μm, d) capsules produced according to Example 1 (PAH-Rho-filled) after drying, image size 40 μm×40 μm, e) capsules having a PAH-Rho/PSS framework after drying, image size 40 μm×40 μm.

Figure 8:
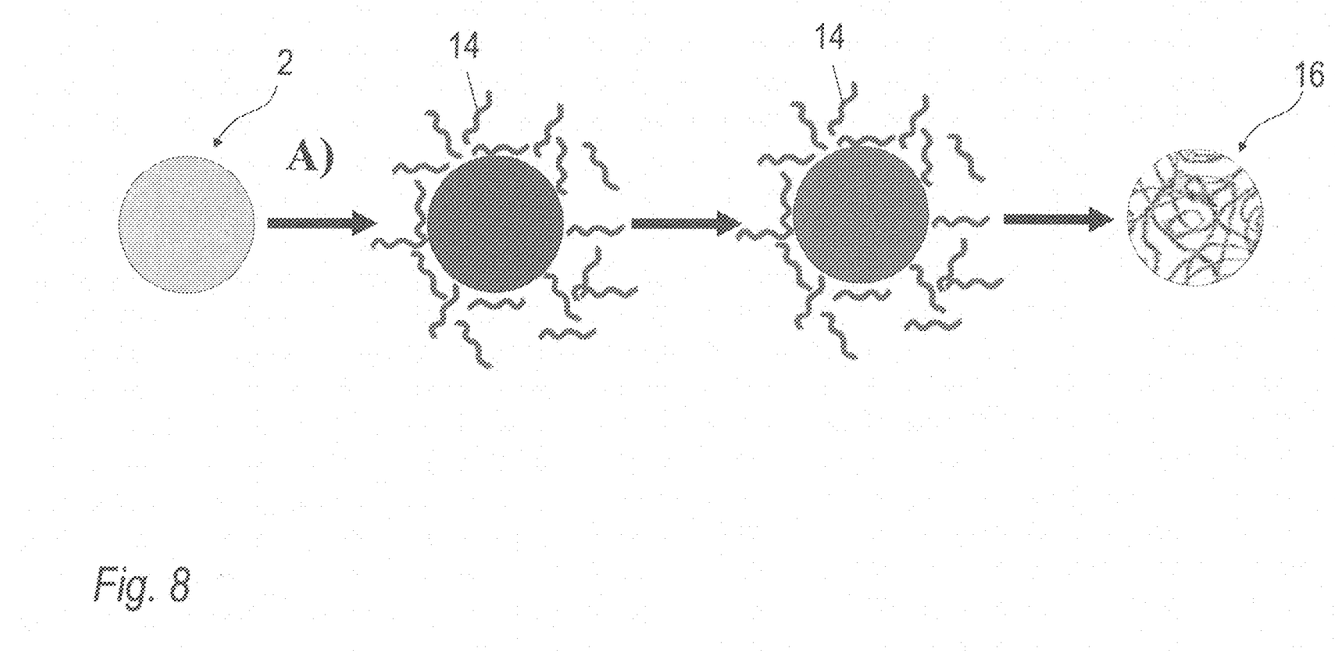
FIG. 8 shows process steps for the production of microtemplates.

FIG. 8 shows individual process steps for the production of microtemplates 16, which consist here of a filigree framework of polyelectrolyte and/or nanoparticle layers 14. For this, porous templates 2 having alternately charged polyelectrolyte and/or nanoparticle layers 14 are filled, i.e. these materials coat the interior surface (pore surface) of the templates 2 and optionally also the exterior surface of the templates. After the dissolution of the templates 2, microtemplates 16 remain, which can be surrounded by partly or largely closed polyelectrolyte and/or nanoparticle layers.

List of Reference Symbols

| | |
|---|---|
| 2 | porous template |
| 4 | active compound |
| 5 | template filled with active compound |
| 6 | primer layer |
| 8 | layers of the capsule shell |
| 9 | capsule shell |
| 10 | CS particle |
| 12, 13 | microcapsules |
| 14 | polyelectrolytes/nanoparticles |
| 16 | inner framework/microtemplate |

Literature

[1] E. Donath, G. B. Sukhorukov, F. Caruso, S. A. Davis, H. Möhwald, *Angewandte Chemie-International Edition* 1998, 37, 2202-2205.

[2] L. Dähne, S. Leporatti, E. Donath, H. Möhwald, *Journal of the American Chemical Society* 2001, 123, 5431-5436.

[3] A. A. Antipov, G. B. Sukhorukov, S. Leporatti, I. L. Radtchenko, E. Donath, H. Möhwald, *Colloids and Surfaces a-Physicochemical and Engineering Aspects* 2002, 198, 535-541.

[4] G. Ibarz, L. Dähne, E. Donath, H. Möhwald, *Advanced Materials* 2001, 13, 1324-1327.

[5] I. L. Radtchenko, G. B. Sukhorukov, H. Möhwald, *Colloids and Surfaces a-Physicochemical and Engineering Aspects* 2002, 202, 127-133.

[6] H. Möhwald, E. Donath, G. Sukhorukov in *Multilayer Thin Films* (Ed.: J. B. Schlenoff), Wiley VCH, New York/Basle, 2003, pp. 363-391.

[7] L. Dähne, C. Peyratout in *Encyclopaedia of Nanoscience and Nanotechnology* Marcel Dekker, Inc., New York 2004

[8] D. G. Shchukin, G. B. Sukhorukov, H. Möhwald *Angewandte Chemie-International Edition* 2003, 42, 4472-4475.

[9] D. V. Volodkin, A. I. Petrov, M. Prevot, G. B. Sukhorukov, *Langmuir* 2004, 20, 3398-3406.

The invention claimed is:

1. A method for the production of core-shell (CS) particles and/or microcapsules, comprising:

providing porous templates, the templates being porous organic and/or inorganic microparticles having a diameter of less than 100 μm;

adsorbing in the porous templates at least one active compound to be encapsulated;

applying at least one primer layer to the porous templates; and forming a capsule shell around the porous templates provided with the primer layer by applying coating materials comprising at least one of alternately charged polyelectrolyte layers and nanoparticle layers to the porous templates, wherein the primer layer is formed from a material which closes pores of the porous templates and is largely impermeable to the coating materials applied in the formation of the capsule shell.

2. The method as claimed in claim 1, wherein the pores have a pore width of 0.3 nm-100 nm or of 1 nm-30 nm.

3. The method as claimed in claim 1, wherein the templates comprise at least one of porous silica particles, porous zeolite particles, and porous polystyrene particles.

4. The method as claimed in claim 3, wherein the porous silica particles range in size from 100 nm to 100 μm or from 500 nm to 30 μm.

5. The method as claimed in claim 3, wherein the porous zeolite particles have a pore width of 0.3 nm to 10 nm.

6. The method as claimed in claim 1, wherein the at least one active compound to be encapsulated comprises at least one of a polymer, a protein, an organic molecule having a molecular weight of over 100 g/mol, a nanoparticle, an enzyme, a catalyst, a dye, a pharmaceutical or cosmetic active compound, and a plant protection agent.

7. The method as claimed in claim 1, wherein at least one auxiliary is used for mediating the adsorption of the at least one active compound.

8. The method as claimed in claim 1, wherein the at least one active compound comprises poly-electrolytes and/or nanoparticles and wherein a surface of the pores is coated by a number of layers of alternately charged poly-electrolytes and/or nanoparticles.

9. The method as claimed in claim 7, wherein the porous templates are prepared in a solution and, additionally or alternatively to the auxiliary, the adsorption of the at least one active compound is controlled by changing the pH of the solution.

10. The method as claimed in claim 1, further comprising dissolving the porous templates after formation of the capsule shell to form the microcapsules.

11. The method as claimed in claim 3, further comprising dissolving silica and/or zeolite templates by fluoride salts in the presence of a buffer solution having a pH between 3.5 and 6.

12. A core-shell (CS) particle having: a diameter of less than 100 μm; a porous core in which at least one active compound is adsorbed; a primer layer which surrounds the porous core; and a capsule shell comprising a number of layers alternately charged polyelectrolyte and/or nanoparticle layers, wherein the primer layer comprises a material which closes pores of the porous core and is largely impermeable to the layers of the capsule shell.

13. The CS particle as claimed in claim 12, wherein the pores of the porous core have a pore width of 0.3 nm-100 nm or of 1 nm-30 nm.

14. The CS particle as claimed in claim 12, wherein the core comprises a porous organic and/or inorganic microparticle having a diameter less than 100 μm.

15. The CS particle as claimed in claim 12, wherein the core comprises at least one of a porous silica particle, a porous zeolite particle, and a porous polystyrene particle.

16. The CS particle as claimed in claim 12, wherein the core comprises a porous silica particle ranging in size from 100 nm to 100 μm or from 500 nm to 30 μm.

17. The CS particle as claimed in claim 12, wherein the core comprises a porous zeolite particle having a pore width of 0.3 nm to 10 nm.

18. The CS particle as claimed in claim 12, wherein the at least one active compound comprises at least one of a protein, a polymer, an enzyme, a catalyst, a dye, and a nanoparticle.

19. A microcapsule having: a diameter of less than 100 μm; a capsule shell comprising a number of layers of alternately charged polyelectrolyte and/or nanoparticle layers; a primer layer on the inside of the capsule shell; and an inner framework of polyelectrolyte complexes and/or polyelectrolyte/nanoparticle complexes, which is surrounded by the primer layer and the capsule shell.

20. The microcapsule as claimed in claim 19, wherein the primer layer and the capsule shell comprise different materials.

21. A method for the production of microcapsules, comprising:
providing at least one porous template, the template being a porous organic and/or inorganic microparticle having a diameter of less than 100 μm;
coating the surface of pores of the porous template with a number of layers of alternately charged poly-electrolytes and nanoparticles;
applying at least one primer layer to the porous template;
forming a capsule shell around the porous template provided with the primer layer by applying coating materials comprising at least one of alternately charged polyelectrolyte and nanoparticle layers to the porous template, the primer layer being formed from a material which closes the pores of the porous template and is largely impermeable to the coating materials applied during the formation of the capsule shell; and
dissolving the porous template.

* * * * *